US008900881B2

(12) United States Patent
Lee (10) Patent No.: US 8,900,881 B2
(45) Date of Patent: *Dec. 2, 2014

(54) QUANTITATIVE ANALYTE ASSAY DEVICE AND METHOD

(76) Inventor: Jin Po Lee, Carlsbad, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 13/199,894

(22) Filed: Sep. 12, 2011

(65) Prior Publication Data

US 2012/0028245 A1  Feb. 2, 2012

Related U.S. Application Data

(63) Continuation-in-part of application No. 12/317,814, filed on Dec. 30, 2008, now Pat. No. 8,455,263.

(51) Int. Cl.
*G01N 33/558* (2006.01)
*G01N 21/78* (2006.01)
*G01N 33/74* (2006.01)
*G01N 21/77* (2006.01)
*G01N 21/64* (2006.01)

(52) U.S. Cl.
CPC ........ *G01N 21/78* (2013.01); *G01N 2021/7796* (2013.01); *G01N 33/558* (2013.01); *G01N 2021/6439* (2013.01); *G01N 33/74* (2013.01); *G01N 2021/7793* (2013.01); *G01N 2021/7786* (2013.01); *Y10S 435/805* (2013.01); *Y10S 435/81* (2013.01); *Y10S 435/97* (2013.01); *Y10S 436/805* (2013.01); *Y10S 436/81* (2013.01); *Y10S 436/811* (2013.01); *Y10S 436/813* (2013.01); *Y10S 436/814* (2013.01); *Y10S 436/818* (2013.01)
USPC .......... 436/514; 422/420; 422/425; 435/7.21; 435/7.23; 435/7.32; 435/287.7; 435/287.9; 435/805; 435/810; 435/970; 436/64; 436/65; 436/525; 436/531; 436/164; 436/169; 436/172; 436/805; 436/810; 436/811; 436/813; 436/814; 436/818

(58) Field of Classification Search
USPC ........ 422/420, 425; 435/7.21, 7.23, 7.32, 7.9, 435/287.7, 287.9, 805, 810, 970; 436/64, 436/65, 514, 525, 531, 164, 169, 172, 805, 436/810, 811, 813, 814, 818
See application file for complete search history.

(56) References Cited

U.S. PATENT DOCUMENTS 5,252,496 A * 10/1993 Kang et al. .................... 436/529
5,384,264 A    1/1995 Chen et al.
(Continued)

FOREIGN PATENT DOCUMENTS

EP    1 879 028 A1    1/2008
WO    WO88/08534    11/1988
WO    WO-00/31539    6/2000

OTHER PUBLICATIONS

Extended European Search Report dated Feb. 4, 2013 in related European Patent Application No. 09836476.3.
Geertruida, et al., "Lateral flow (immuno)assay: its strengths, weaknesses, opportunities and threats. A literature survey," Anal. Bioanal. Chem., (2009), 393:569-582.

(Continued)

*Primary Examiner* — Chris L Chin
(74) *Attorney, Agent, or Firm* — Foley & Lardner LLP; Yang Tang (57) ABSTRACT

The present invention relates to a quantitative assay device and a method for the determination of an analyte, based on a test strip, which contains a porous test membrane allowing for capillary flow of the analyte and complexes of the analyte, a porous upstream membrane in fluid connection with the test membrane and a porous downstream membrane in fluid connection with the test membrane, wherein the test membrane contains two bands having deposited on there high and low concentrations of different calibrator agents and a test band capable of reacting with conjugated analyte complexes giving rise to a measurable signal.

14 Claims, 2 Drawing Sheets

(56) References Cited

U.S. PATENT DOCUMENTS

| | | |
|---|---|---|
| 6,528,323 B1 | 3/2003 | Thayer et al. |
| 2003/0119203 A1 | 6/2003 | Wei et al. |
| 2005/0112780 A1 | 5/2005 | Song |
| 2006/0246513 A1 | 11/2006 | Bohannon |
| 2007/0087451 A1 | 4/2007 | Kirkegaard et al. |
| 2008/0125582 A1 | 5/2008 | Millan |

OTHER PUBLICATIONS

International Search Report and Written Opinion in related PCT Patent Application No. PCT/US09/06297.

EP Office Action dated Apr. 10, 2014 in related EP Patent Appl No. 09836476.3.

* cited by examiner

QUANTITATIVE ANALYTE ASSAY DEVICE AND METHOD

CROSS REFERENCE TO RELATED APPLICATIONS

This application claims the benefit of U.S. application Ser. No. 12/317,814 filed Dec. 30, 2008 now U.S. Pat. No. 8,455,263 of which this application is a continuation in part.

FIELD OF INVENTION

The present invention relates to methods and devices for assaying biological fluid samples and particularly bodily fluid samples. More particularly the invention relates to methods and devices for detecting and quantitatively measuring the concentration of an analyte in a sample.

BACKGROUND

Quantitative analysis of fluid samples including antigens, antibodies hormones, and other secreted proteins as well as other types of proteins frequently provides critical diagnostic data. The concept of immunoassays is well known in the art and is based on reagent impregnated capillary membranes in which an immobilized reagent in the detection zone of the strip binds to analytes conjugated with visual label such as a latex particle or metal containing compounds. In addition U.S. Pat. Nos. 3,654,090, 3,791,392 and 3,817,838 disclose enzyme labels and the means to detect such, and U.S. Pat. No. 4,062,733 discloses radioactive labels. Preferred labels are derived from metal sols. Labels such as prepared from a gold sol are bound to a ligand capable of further binding or conjugating to an analyte or other ligand or antibody. Test strips have been used in qualitative assays in a large number of applications involving analytes contained in such bodily fluids as urine and blood. Probably the earliest and most common use of assays is in detecting human chorionic gonatropin as an indicator of pregnancy in humans. These assay devices are based on test strips where the assay is performed and results read in a single step, e.g. where the liquid sample is placed onto a porous. membrane, any analyte of interest therein binds a corresponding ligand, and the results are indicated visually in a detection zone separate from the sample loading zone through formation of a specific complex. The test strips are normally contained in a dipstick or cassette allowing the user to conduct the test without any additional equipment. Such devices are disclosed in U.S. Pat. Nos. 4,235,601, 4,235,601 and 5,384,264. Assay devices that can be used with whole blood are disclosed in U.S. Pat. No. 5,821,073.

Known assay devices generally involve a sandwich assay or a competitive assay. In a sandwich assay, analyte of interest present in a fluid sample interacts with a ligand bound label or tracer resulting in a complex of analyte and label. This can occur prior to adding the analyte to the test strip or the label bound ligand can be removably deposited on the porous membrane forming the test strip. The test strip allows the label-bound analyte to move by capillary action to a sample capture zone where the analyte complex is retained by virtue of being bound to the immobilized capture ligand normally an antibody to the analyte. In the case of a gold label the presence of the analyte is indicated by color formation at the analyte test zone. Preferably the assay device also contains a second immobilized ligand band, generally identified as a control band capable of binding to label ligand even in the absence of an analyte, to show that the strip is functioning properly.

In a competitive or inhibition assay both the analyte and the label ligand are capable of reacting with the immobilized ligand in the sample capture zone and thus, both the analyte and the label bound ligand compete for attachment to the immobilized ligand in the sample capture zone. Any analyte present would displace the binding of a labeled ligand. The presence of a signal in the sample capture zone would thus indicate a negative result.

Most of the assay devices based on test strips determine the presence or absence of an analyte but do not provide but a very rough measure of the quantity of an analyte present in fluid sample. Even those that give a quantitative measurement by incorporating a standard in the test device suffer from inaccuracies resulting from temperature, air moisture, flow time variations, strip to strip variations and signal strength variations. These and other deficiencies of the prior art assay devices are overcome by the chromatographic assay device of the present invention, which provides a rapid effective, and efficient quantitative analysis of fluid samples.

SUMMARY OF THE INVENTION

The present invention provides an assay device for and a method of measuring the amount of an analyte in a fluid sample using a solid phase chromatographic assay, such as a sandwich assay, in which one or more analyte of interest is bound to a label conjugate and is also bound to a capture reagent in a test band as part of a specific binding pair. In addition to the test band, the microporous test strip membranes of the present invention contain at least two different standard bands of immobilized calibrator agents capable of binding to their own pair label reagents. The labeled reagents captured at the standard bands by the calibrator agents are used to create a template against which to measure the concentration of an analyte in a sample bound in the test band. The immobilized calibrator agents in the standard bands are contacted with the corresponding label reagents as the fluid sample passes through the assay strip. Any analyte of interest present in the fluid sample is bound at the sample capture band. Based on the relative intensity of the label bound in these bands an accurate concentration of analyte can be obtained. Thus the density or intensity of a label such as a gold sol conjugate in the various sample capture bands on the membrane strip reflects the amount of the analyte present as do the standard bands which then reflect the density of the calibrator agent bound and which has a known concentration. It is critical to an determination of the exact concentration of the analyte in the sample that the correct amount of calibrator agent be immobilized within a standard deviation of less than 0.05%. Commercially available optical readers can then convert the reflected light intensity of the sample into concentration as measured on the basis of the curve derived from the reflected intensity of the standard bands of known concentrations. A competitive assay, in which the analytes of interest is competitive with a capture reagent in the test band to a label conjugate as part of a specific binding pair. The assay device of the present invention can be used to measure the concentration of analytes contained in any liquid sample including blood, urine, water and oils.

The present invention. comprises a lateral flow assay method and system including a test strip and/or a cassette for holding the test strip, for determination of the presence and/or quantity of analytes in samples, including but not limited to biological or other samples containing materials including antigens, antibodies, hormones and other secreted proteins, cell surface proteins, transmembrane proteins, glycoproteins, enzymes, proteins associated with cells and other proteins, proteins associated with pathogens such as bacteria, viruses, and fungi, carbohydrates, drugs, peptides, toxins, nucleic acids, small molecules, and aptamers. This novel assay or system can detect and/or quantitate analytes in small volumes of samples. Generally, the sample volume is less than about 100 µl. Most preferably, the sample volume is about 40 µl. This assay or system can also separate cells from fluid in a sample, such as red blood cells or white blood cells or other cell types. The assay or system also provides low background noise and is highly efficient.

DETAILED DESCRIPTION OF INVENTION

Figure 1:
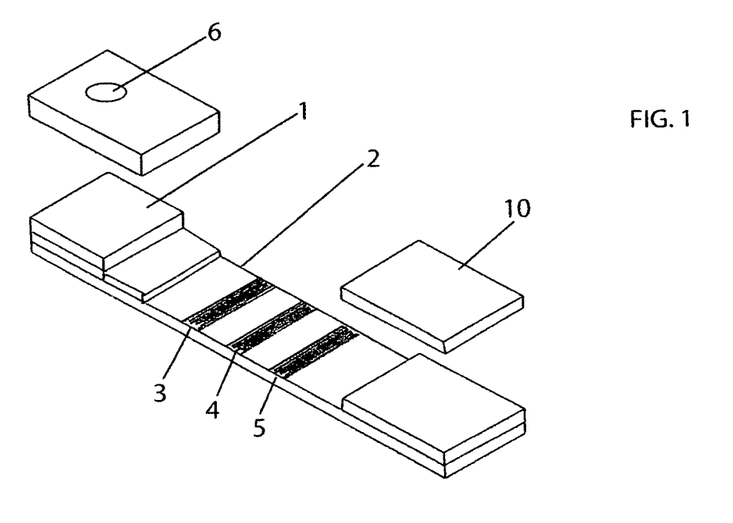
FIG. 1 is an exploded view of the test strip of the invention.
Figure 2:
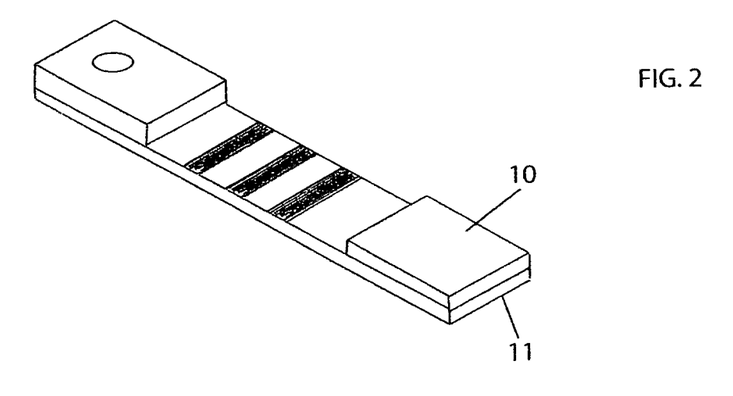
FIG. 2 is a perspective view of a test strip of the invention
Figure 3:
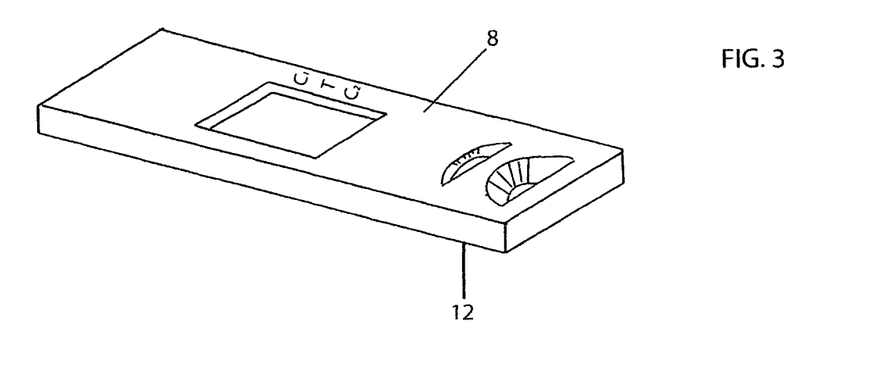
FIG. 3 is a perspective view of a cassette device of the invention.
Figure 4:
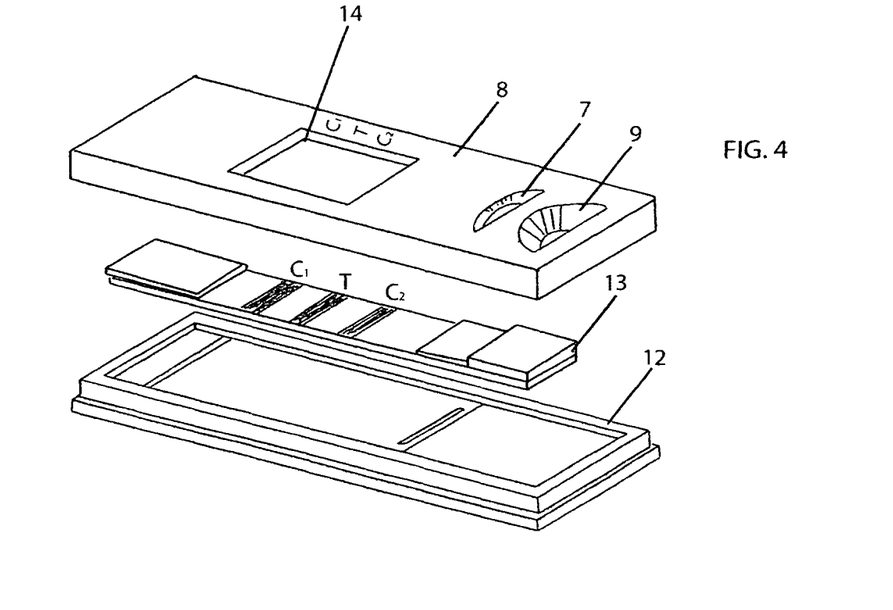
FIG. 4 is an exploded view of a cassette device of the invention

A test strip constructed in accord with the invention for the use with whole blood samples is shown in FIGS. 1-4. A red or white blood cell layered mesh trap 1 is shown as overlying a sample introduction membrane 6 and 13 that also contains downstream from the sample addition point 7 the label ligands required to bind at the test zone 4 and at the calibrator or standard bands 3 and 5 on the microporous test membrane 2. Access to cell trap 1 for application of test sample is obtained through opening 7 in cover 8 in FIGS. 3 and 4. The test strip 2 also includes a terminal sample flow zone 10 distal to the test and standard zones. Each of the above mention zones are in fluid communication with each other. All of the components described with respect to the test strip of invention may be encased in a fluid tight housing composed of a solid plastic cover 8 with view window 14 which fits tightly over solid plastic base 12 as shown in FIG. 3. Opening 9 in the cassette cover allows for the introduction of a buffer or other solution aiding in the capillary flow of the sample.

For ease of understanding, the following definitions will apply throughout this description:

1. The term "antigen" as used herein refers to any analyte, which is capable of binding antibodies. Antigens may comprise, without limitation, chemical compounds, polypeptides, carbohydrates, nucleic acids, lipids, and the like, including viral particles, viral subunits, bacterial and parasite surface antigens, and host proteins that may be diagnostic of the subject's condition.

2. A "binder" refers to a ligand for the analyte as in the format of a sandwich assay, or a ligand for both the analyte and the tracer or label as in the format of a competitive assay. A binder can be chosen from a group of molecules or compounds capable of binding the analyte, such as an antigen to the antibody analyte, or an antibody to the antigen analyte.

3. A "test zone or band" refers to an area in which a binder or the analyte is attached, movably or immovably, such as to the analyte test strip portion of an assay device.

4. The term "test strip" or "assay strip" refers to a porous membrane capable of capillary flow of the fluid sample containing the bound analytes and other antigens involved in the determination of the analyte concentration. Common porous membranes are fiberglass, porous nitrocellulose or polyethylene. An "analyte test strip" of the invention consists of, collectively, all of the zone supporting membranes and any filters of the assay device.

5. A "tracer" refers to a ligand for the analyte or the binder labeled with a detectable label, preferably a visually readable particulate label, such as colloidal gold, latex and liposomes including dye, carbon black, and the like.

6. A "sample loading or application zone" refers to an area of an analyte test strip on which a fluid analyte sample is applied for migration to the test bands.

7. A "fluid analyte sample" can be any fluid suspected of containing analyte of interest for which a particular assay is specific. Test sample may represent any body fluid, including urine, blood, sweat, lymph, intraperitoneal fluid, crude tissue extract or homogenate, derived from a fetus, neonate, juvenile or adult subject; a non-biological fluid such as water from some ecological niche, e.g., a river or a lake; or a solution used in a laboratory.

8. A "label" is a molecule or compound, which directly or indirectly mediates the formation of a signal (such as a color change), which is used in assay to indicate the presence, absence or concentration range of analyte of interest in a test sample. Labels may include enzymes, fluorescers, liposomes, erythrocyte ghosts, polymer microcapsules, color polymer particles (latex), and preferably includes sols of metal-containing compounds. A wide variety of patents and patent applications provide an extensive literature of different techniques for producing detectable signals in immunoassays. The following list of United States patents is merely illustrative of the type of label which can find application in this invention: U.S. Pat. No. 3,646,346 discloses radioactive labels; U.S. Pat. Nos. 3,654,090, 3,791,932, and 3,817,838 disclose enzyme labels; U.S. Pat. No. 3,996,345 discloses fluorescer-quencher labels; U.S. Pat. No. 4,062,733 discloses radioactive label; U.S. Pat. No. 4,067,959 discloses fluorescer or enzyme label; U.S. Pat. No. 4,104,099 discloses chemiluminescent label; and U.S. Pat. No. 4,160,645 discloses non-enzymatic catalyst label. U.S. Pat. No. 3,966,879 discloses an electrophoretic technique employing an antibody zone and U.S. Pat. No. 4,120,945 discloses a radioimmune assay (RIA) where labeled analyte is initially bound to a solid support through antibody. U.S. Pat. No. 4,233,402 discloses enzyme pair labels; U.S. Pat. No. 4,720,450 discloses chemically induced fluorescent labels; and U.S. Pat. No. 4,287,300 discloses enzyme anionic charge labels.

Labels can also be metal-containing sols; i.e., metal or metal compounds such as metal oxides, metal hydroxides, metal salts, metals or metal-containing compounds mixed with polymers or coated onto polymer nuclei. These metal labels may include dry forms of any of the above-named metal or metal compound sols, and preferably include colloidal gold in dry form.

"Label response" refers to the signal strength that is generated by the label when it becomes attached to the reagents immobilized in the test or standard bands. With color generating labels reflective light units are a preferable way of measuring label response.

9. A "complex" means (depending on the context) any multimolecular complex formed by analyte and one or more ligands, or by labeled ligand and immobilized ligand. In a sandwich-type immunoassay, e.g., the following complexes occur: analyte/labeled ligand duplex first produced in the assay (first complex) and analyte/labeled ligand/immobilized ligand triplex formed second in the assay (second complex).

10. "Fluid communication" refers to structures which are in contact with, but not necessarily affixed to one another and which allow the passage of a fluid from one to the other.

11. "Assay" refers to several different types of assay formats in which an analyte of interest can be detected using an assay analyte test strip. For example, in a sandwich-type immunoassay, analytes of interest in the analyte sample, when present, bind a labeled tracer movably incorporated in the analyte test strip (consisting of a porous membrane) at the tracer zone to form a first complex. The tracer is a molecule, which binds the analyte of interest and is conjugated to a label, preferably a metal label, and most preferably colloidal gold.

12. The term "test band" or "test zone" as used herein refers to a region or zone on the chromatographic assay strip that contains at least one analyte binding agent. The analyte binding agent is usually immobilized in a band or zone such that after reaction with a detectable agent, the band or zone produces an observable or measurable result reflecting the presence or amount of analyte present in the sample. The "test band" may be comprised of more than one capture zone for capturing more than one analyte in the sample, in which event, more than one analyte binding agent may be used. For example, two assay combinations that are considered to be within the scope of the invention are assay combinations that simultaneously detect hepatitis C virus. (HCV) and human immunodeficiency virus (HIV), and assay combinations that simultaneously detect Hepatitis B surface antigen (HBsAg) and *Treponema pallidum* antigen (TP). Still other combinations are possible and are within the scope of the invention.

13. The term "conjugate" and "detectable agent" are used interchangeably herein to refer to an antibody or an antigen that is conjugated to a detectable material such as a colored agent, a fluorescent agent, an enzyme agent or a chemiluminescent agent. In the practice of the present invention, the "conjugate" or "detectable agent" specifically binds the analyte to be determined or the captured analyte immobilized on the capture band. Optionally, the "conjugate" or "detectable agent" produces a measurable quantitative reading at the capture band that reflects the amount of an analyte present at the capture band. As described further below, the direct measurable quantitative density in the capture band does not necessarily reflect the amount of an analyte present at the capture band through binding, but the intensity of band as measured by reflective light units (RLU) does reflect the amount of an analyte present at the capture band.

14. The term "standard band" or "calibrator band" as used herein contains calibrator agents immobilized in calibrator binding zones on the test strip. The calibrator agents bind specifically to calibrator binding agents to form a calibrator binding pair. The present invention includes two or more calibrator bands. An advantage to having calibrator binding pairs is that they act as internal standards, that is, the calibrator against which the amount of an analyte present at the capture band may be calculated. The calibrators may be used to correct for strip to strip variability. One of the calibrators can be designated a high calibrator ("HC") and the other of the calibrators can be designated a low calibrator ("LC"). The reflection density of HC and of LC, can be used to determine the standard curve. It is also within the scope of this invention to use more than standard bands all of different concentrations of he xcalibrator agent. The standard curve is made for each quantitative assays by using the RLU values of the calibrator agents to generate a regression equation to describe the relationship between two variables. Although, in general, any conventional calibrators can be used herein, it is generally preferred to use as calibrators compounds that do not exist in the sample or do not immunologically cross-react with compounds that exist in the sample; for example, monoclonal antibody against rabbit immunoglobulin, monoclonal antibody against bovine thyroid globulin, or antibody against 2,4-dinitrophenylated bovine serum albumin (BSA-DNP), which can be purchased from Molecular Probes (Eugene, Oreg., cat# A-23018) can be used as the two points of calibrator reagent. The compound 2,4-dinitrophenol (DNP) is a small molecule which does not exist within the human body but acts as a hapten; that is, it is immunogenic when conjugated to a larger molecule such as a protein carrier and injected into an antibody-producing mammal such as a mouse, a rat, a cow, a rabbit, a horse, a sheep, or a goat.

The test devices of the present invention comprise test strips, which may be enclosed in a cassette for easier use. Such test strips enclosed in such cassettes are described in U.S. Pat. Nos. 5,821,073 and 5,384,264, the disclosures of which are hereby incorporated by this reference. The test strips employed in the present invention generally comprise a porous test membrane of sufficient porosity to allow the components of the test including the analyte and its complexes to flow through the membrane by capillary action. Preferred membranes are porous nitrocellulose, porous. polypropylene and paper membranes. Such membranes are well known in the art. These membranes contain immobilized ligands capable of binding the analyte in a test zone, preferably in the form of a band across the width of the test membrane as well as the HC and LC calibrator agents in separate zones across the width of the test membrane in the calibrator are standard bands. As indicated the immobilized ligands used for the test and calibrator zones are different. Known amounts of calibrator agents are immobilized in the standard bands to establish the base line for the quantitative determination of the analyte. The remaining active sites after the application of the ligands in the various zones on the membrane are blocked to allow free flow of the analyte, analyte complexes, labeled ligands and labeled ligand complexes through the test strip.

In addition to the porous membrane the test strips of the present invention contain a second porous membrane upstream from the first membrane but in fluid communication with the test membrane containing the immobilized ligand bands. The upstream membrane is of an inert type in that it does not contain sites, which would bind ligands flowing through the membrane. Such membranes are preferably made of unwoven fiberglass or polypropylene, again of sufficient porosity to allow capillary flow of analyte, analyte complexes and labeled ligands. These membranes can also be suitably used to separate the analyte to be tested from components in the sample, which could interfere in the analysis of the analyte. Thus in the analysis of blood the red and white blood cells can be separated from the fluid serum containing the analyte to be tested. The upstream membrane therefore contains a site for the application of the sample, and in addition contains the labeled ligands, downstream from the application site and upstream from the contact with the test membrane, that react with the analyte in a sandwich assay or with the bound ligand in the test zone in a competitive assay, as well labeled ligands that complex with the bound calibrator ligands in the standard bands. The labeled reagents are deposited on the upstream membrane in a manner that they can lift of from the membrane when contacted by the fluid sample and in the case of the analyte react with the analyte to form a complex that can then continue to flow from the upstream membrane into the test membrane.

The test strip further contains a third membrane, in fluid connection with the test membrane, at the downstream end of the test membrane capable of absorbing the fluid sample that has passed through the test membrane and that acts as the driving force to cause the fluid sample to flow through the test membrane by capillary action. Such adsorption pads are preferably made of high absorbency materials such as paper that are capable of absorbing the sample and any buffer added to the strip.

The operation of the assay of the present invention basically involves the addition of a known quantity of a fluid sample containing a suspected analyte to the device at the sample application site using a transfer pipette. Generally the amount of sample will be in the range of 10 to 100 microliters. Usually when the test strip is incorporated into a cassette, a sample well is provided for the addition of the sample to the test strip. The sample is absorbed by the upstream membrane and drawn by capillary action through such upstream membrane towards the test membrane. In the process the sample passes through the region of the upstream membrane where label bound ligands are removably deposited. In addition to the label ligand that binds to the analyte if present the upstream membrane also contains high and low calibrator label ligands removably deposited on the upstream membrane. In a preferred embodiment the two calibrator label ligands and the label ligands used to bind to the analyte to be tested the sample are mixed and in dry form.

In the case of the sample being blood the upstream membrane can also act as a filter to filter out the red and white blood cells but let the serum or plasma pass through. The flow of the sample through the test strip is frequently facilitated by the addition of a buffer. In general the amount of buffer added is at least equal to but no more than five times the quantity of the fluid sample. Suitable buffers include any pharmaceutically acceptable aqueous buffer, which will not react with the test sample of the other test and control ligands of the test strip. In general phosphate buffers, based on mono and di sodium hydro phosphate and commercially available, are preferred although other buffers such as citrate buffers or Ringer's solution may also be used.

The sample stream picks up the label ligands for both the test and standard bands before contacting the test membrane. The preferred labels of the present invention are those that give rise to color complexes in the test and standard bands. Although color resulting from enzyme bound ligands or latex bound ligands which have been used in conjunction with qualitative assays using capillary flow of test strips such as disclosed in the above mentioned patents and others can be used in the assays of the present invention, the preferred color forming ligands are gold conjugates that can bind to the desired analyte to be analyzed and to the calibrator agents. The quantitative assay of the present invention is based on the color intensity of an analyte sample and the color intensity generated by the calibrator agents in the standard bands. Thus in sandwich assay, the higher the amount of analyte in the test sample, the more label ligands binds to the analyte and the higher the amount of label ligand/analyte complex that will bind to the to the immobilized ligand in the test zone, increasing the label intensity in the band. Thus label intensity increases with increasing amount of analyte present in the sample. In a competitive assay, the higher the amount of analyte in the test sample, the less label ligand can bind to the immobilized ligand-BSA (analyte-BSA) in the test zone, decreasing the label intensity in the test zone. Thus label intensity decreases with increasing amount of analyte present in the sample. However in order to accurately establish the actual concentration of the analyte, factors other than analyte concentration must be excluded from any quantitative determination. It is for that purpose that the test strips of the present invention employ the calibrator agents in the standard bands which then provide the means for an accurate quantitative determination. Preferably and for higher accuracy the present invention employs at least two different calibrator agents in separate standard zones, before and after the test zone on the test membrane. Since a fixed amount of the calibrator agent is immobilized in the standard zones and an excess of the calibrator label conjugate is deposited in the upstream band, the same intensity of color is generated in the standard bands at any given time interval time during the test for different test strips made in the same way. Using the relative light units a standard curve can be obtained for each high and low calibrator zone, which then serves as the base for the determination of the quantitative amount of analyte present. Although, in general, any conventional calibrators can be used herein, it is generally preferred to use as calibrators agents that do not exist in the sample or do not immunologically cross-react with compounds that exist in the sample; for example, 2,4-dinitrophenylated bovine serum albumin (BSA-DNP), which can be purchased from Molecular Probes (Eugene, Oreg., cat# A-23018) can be U.S.ed as the calibrator reagent. The compound 2,4-dinitrophenol (DNP) is a small molecule which does not exist within the human body but acts as a hapten; that is, it is immunogenic when conjugated to a larger molecule such as a protein carrier and injected into an antibody-producing mammal such as a mouse, a rat, a cow, a rabbit, a horse, a sheep, or a goat. Immobilized ligands in the low calibrator standard zone are for example monoclonal antibody against bovine thyroid globulin (BTG) and immobilized ligands in the high calibrator standard zone are for example goat anti-rabbit IgG proteins. Conjugates used with the immobilized ligands are goat BTG gold antigens and rabbit IgG gold antigens.

In order to determine the amount of the analyte present it is necessary to develop the relationship of color intensity in the test zone with concentration of analyte in a sample. Such relationship, plotted as a curve, is obtained by preparing a solution or dispersion of the analyte to be tested at a known high concentration and then continuously diluting the test solution or dispersion and measuring the change in color intensity in exposed test strips. Obviously this curve will also be different at different time intervals. However these curves can be correlated with the standard curves obtained from the calibrator agents for known concentrations in the case of measurement of a sample containing an unknown amount of analyte. Thus in each test of an unknown sample three different color intensities are obtained. The intensities of the standard band can be correlated to the standard concentration curves for the analyte and a quantitative value for the analyte in the sample to be tested calculated. For verification purposes it is desirable to obtain relative light units for two exposure times, which can be correlated to the standard values of concentration vs. label response in reflectance units to obtain a verification of the concentration of the analyte in the sample. The reliability of the curve depends in large part on the accuracy and strip to strip consistency of the binding agent in the standard bands. Such accuracy and consistency is accomplished by using linear motion displacement pumps that provide digitally controlled pulse free linear flows as are available from the IVEK corporation.

Although the necessary calibration of the standard strips and concentration calculations can be carried out manually, they are preferably embodied in software that can be read by commercial equipment capable of measuring the color intensity of the test band and the standard bands. The color intensity data points generated by the standard bands and known concentrations of analyte in the test band can be incorporated into a memory device such as an electro-magnetic card or an RFID card. When such card is inserted into a commercially available optical camera reader, such as manufactured by Kaiwood Technology Co. together with a cassette that has been treated with a sample, the reader can provide the concentration of any analyte in the sample.

In general analytes and the corresponding complex forming antibodies, or antigen if the analyte is an antibody, are known in the art from the development of qualitative assays for such analytes, as are the label conjugates that will bind to the analyte. For example, if the lateral flow assay is intended to measure hepatitis B virus ("HBV") surface antigen (HBsAg) in a blood sample, the capture band will contain antibody to HBsAg immobilized on the test membrane at the test band.

Suitable analytes include, but are not limited to antigens, antibodies, hormones, drugs, cell proteins, DNAs, cardiac markers, tumor or cancer markers, autoimmune disease markers, or any macromolecule that could raise antibodies. When the analyte is an antigen, the antigen can be an antigen associated with an infectious agent. The infectious agent can be a virus, a bacterium, a fungus, or a prion. When the infectious agent is a virus, the virus can be selected from the group consisting of HIV, hepatitis virus A, B, C, and D, herpes simplex virus, cytomegalovirus, papilloma virus, Ebola vir, SARS virus Rhinovirus, and Vaccinia virus, but is not limited to those viruses. When the infectious agent is a bacterium, the bacterium can be a gram-positive bacterium or a gram-negative bacterium. The bacterium can be selected from the group consisting of *Bacillus anthracis, Escherichia coli, Helicobacter pylori, Neisseria gonorrheae, Salmonella* species, and *Shigella* species, but is not limited to those bacteria. When the infectious agent is a fungus, the fungus can be a *Mycosporum* species or an *Aspergillus* species, but is not limited to those fungi.

When the analyte is a hormone, typically it is selected from the group consisting of hCG, thyroxin, TSH, glucagons, insulin, relaxin, prolactin, luteinizing hormone, melanotropin, somatotropin, follicle-stimulating hormone, gastrin, bradykinin, vasopressin, and other releasing factors; however, other hormones of physiological or pathological interest can be the analyte.

When the analyte is a cancer or tumor marker, typically it is selected from the group consisting of prostate specific antigen (PSA), carcinoembryonic antigen (CEA), and α-fetoprotein; however, other cancer or tumor markers can be the analyte.

When the analyte is a cardiac marker, the cardiac marker is typically selected from the group consisting of Troponin-I, Troponin T, Creatine kinase-MB isoforms (CK-MB), myoglobin, C-reactive protein (CRP), fatty acid binding protein (FABP), glycogen phosphorylase isoenzyme BB (GPBB), B-type natriuretic peptide (BNP) and pro-BNP; however, the analyte can be another cardiac marker.

The invention is further illustrated but not limited by the following examples.

EXAMPLE 1

Onto a test strip comprising a porous nitrocellulose strip (7.5 cm×0.7 cm) as the test membrane sufficient monoclonal antibody against human prostate specific antigen (PSA) is immobilized in a test band to give rise to measurable color intensity when complexed with PSA analyte color conjugates that can be expected in a sample. In separate experiments the relationship of color intensity and concentration is established as a curve. Rabbit IgG and bovine thyroid globulin are immobilized in two standard bands by using an IVEK ceramic linear pump having an accuracy of 99.95%, in known amounts sufficient to give rise to a color intensity corresponding to PSA at concentration of 1 and 10 nanogram per milliliter (ng/ml) respectively when such is complexed with a gold label monoclonal PSA specific antibody. The test membrane is dried in a dehumidifying chamber (humidity of 10-15%) overnight. Excess of the gold label antibody against PSA, gold label monoclonal antibody against rabbit IgG and gold label monoclonal antibody against bovine thyroid globulin are also removable deposited in an upstream fiberglass membrane. The conjugate fiberglass pad is treated with a buffer to neutralize interfering sites and then vacuum dried at 2 Torr overnight at room temperature. The pad was then cut into narrow strips (1×0.7 cm). The bands are arranged such that the sample first contacts the low calibrator band showing the color intensity with the gold conjugate corresponding to 1 ng/ml of PSA antigen, then the test band, followed by the high calibrator agent band, capable of binding the equivalent of 10 ng/ml of PSA. The correlation of the color intensity in RLU units with analyte concentration, lot #, test time, slope and intercept for the two standard bands of the particular test strip is loaded into a RFID memory card. The antigen concentrations can then be calculated using the equation $Y=AX+B$ where Y is the concentration of the analyte, X is the color intensity generated by the sample in RLU units, A is the slope of the curve obtained from the standard values and B is the intercept of the test value on the curve. The test membrane is in fluid connection with an upstream non-woven fiberglass membrane onto which is deposited the antibody to the PSA antigen conjugated to a gold label by techniques known in the art. The label conjugate is deposited down stream from where the sample to be analyzed is added to the upstream fiberglass membrane. The assay test strip also contains a sample absorption pad in fluid connection with the downstream end of the test membrane. The test strip is inserted into a cassette such as described in U.S. Pat. No. 5,821,073.

One drop of blood suspected of containing the PSA analyte, approximately 30 microliters, is added to the sample applicator site on the upstream fiberglass membrane followed by four drops, about 200 microliters, of a commercially available phosphate buffer. The fiberglass membrane is sufficiently dense to filter out the red and white blood cells but will let the serum pass. The serum of the blood combined with buffer flows through the upstream membrane by capillary action to the label conjugate redistributing the gold antibody conjugate in the serum which then forms a complex with any analyte present in the sample. The buffer diluted serum passes from the fiberglass membrane to the porous nitrocellulose membrane and continues to flow by capillary action through the nitrocellulose membrane. Analyte gold conjugate complex is captured by the PSA antibody deposited in the test band and gives rise to a reddish color the intensity of which corresponds to the amount of analyte present in the sample. Monoclonal antibody against rabbit IgG and monoclonal antibody against bovine thyroid globulin gold conjugate removably deposited on the fiberglass membrane and contained in the sertum are also captured by the high and low standard bands containing sufficient calibrator agent to capture the equivalent of either one or ten ng/ml of analyte. In the presence of PSA analyte in the sample three bands of differing color intensity are obtained. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The photo-camera reader employed, Kaiwood CHR 100, is capable of converting the color intensity into concentration using the data on the memory card. Color intensities were measured 10 and 15 minutes after the addition of the sample and buffer. The following results are obtained:

10 Minutest Test Result:

| Analytes | PSA Concentration | RLU |
| --- | --- | --- |
| Calibrator H | 10 ng/ml | 10 |
| Calibrator L | 1 ng/ml | 1 |
| Sample | Y | 4.04 |

Based on the two point standard curve, the reader showed 4 ng/ml of the PSA antigen (Y) in the sample.

15 Minutes Test Result:

| Analytes | PSA Concentration | RLU |
| --- | --- | --- |
| Calibrator H | 10 ng/ml | 23.9 |
| Calibrator L | 1 ng/ml | 10.3 |
| Sample | Y | 19.49 |

Based on the two point standard curve, the reader showed 4 ng/ml of PSA antigen (Y) in the sample.

EXAMPLE 2

In a procedure similar to that of Example 1, onto a test strip comprising a porous nitrocellulose strip (7.5 cm×0.7 cm) as the test membrane containing sufficient monoclonal antibody against human thyroid stimulate hormone antigen (TSH) is immobilized in the test band to give rise to a measurable color intensity at TSA concentrations that can be expected in the sample. In separate prior experiments the relationship of TSH concentration and color intensity is established. Rabbit IgG and bovine thyroid globulin are immobilized in two standard bands by using an IVEK dispensing linear pump, in amounts sufficient to give rise to a measurable color intensity corresponding to TSH at concentrations of 5 µIU/ml and 20 µIU/ml respectively when complexed with a gold label monoclonal TSH. The test membrane is dried in dehumidifying chamber (humidity: 10-15%) overnight. Excess of the gold label antibody against TSH, gold label monoclonal antibody against rabbit IgG and gold label monoclonal antibody against bovine thyroid globulin are also removably deposited in an upstream fiberglass membrane. The conjugate fiberglass membrane was then treated with a conjugate buffer to neutralize any interfering sites and then vacuum dried at 2 Torr overnight at room temperature. The pad was then cut into (1×0.7 cm) strips. The bands are arranged such that the sample first contacts the low calibrator band showing the color intensity with the gold conjugate corresponding to 5 µIU/ml of TSH antigen, then the test band, followed by the high calibrator agent band, capable of binding the equivalent of 20 µIU/ml of TSH. The correlation of the color density in RLU units with analyte concentration, lot #, test time, slope and intercept for the two standard bands of the particular test strip is loaded into a RFID memory card. The antigen concentrations can then be calculated using the equation Y=AX+B where Y is the concentration of the analyte, X the color intensity generated by the sample in RLU units, A is the slope of the curve obtained from the standard values and B is the intercept of the test value on the curve.

The test membrane is in fluid connection with an upstream non-woven fiberglass membrane onto which is deposited the antibody to the TSH antigen conjugated to a gold label by techniques known in the art. The label conjugate is deposited down stream from where the sample to be analyzed is added to the upstream fiberglass membrane. The assay test strip also contains a sample absorption pad in fluid connection with the downstream end of the test membrane. The test strip is inserted into a cassette such as described in U.S. Pat. No. 5,821,073.

One drop of blood suspected of containing the TSH analyte, approximately 30 microliters, is added to the sample applicator site on the upstream fiberglass membrane followed by four drops, about 200 microliters, of a commercially available phosphate buffer. The fiberglass membrane is sufficiently dense to filter out the red and white blood cells but will let the serum pass. The serum of the blood combined with buffer flows through the upstream membrane by capillary action to the label conjugate redistributing the gold antibody conjugate in the serum which then forms a complex with any analyte present in the sample. The buffer diluted serum passes from the fiberglass membrane to the porous nitrocellulose membrane and continues to flow by capillary action through the nitrocellulose membrane. Analyte gold conjugate complex is captured by the TSH antibody deposited in the test band and gives rise to a reddish color the intensity of which corresponds to the amount of analyte present in the sample. Monoclonal antibody against rabbit IgG and monoclonal antibody against bovine thyroid globulin gold conjugate removably deposited on the fiberglass membrane and distributed in the serum are also captured by the high and low standard bands containing sufficient calibrator agent to capture the equivalent of either 5 or 20 5 µIU/ml of analyte. In the presence of TSH analyte in the sample three bands of differing color intensity are obtained. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The photo-camera reader employed, Kaiwood CHR 100, is capable of converting the color intensity into concentration using the data on the memory card. Color intensities were measured 15 minutes after the addition of the sample and buffer. The following results are obtained:

15 Minutest Test Result:

| Analytes | TSH Concentration | RLU |
| --- | --- | --- |
| Calibrator H | 20 µIU/ml | 102 |
| Calibrator L | 5 µIU/ml | 47 |
| Sample | Y | 19.5 |

Based on the two point standard curve, the reader showed 0.78 µIU/ml of the TSH antigen (Y) in the sample.

EXAMPLE 3

The procedure of Example 1 is repeated to determine the concentration of human carcinoembryonic antigen (CEA) with gold label monoclonal specific anti bodies. In separate prior experiments the relationship of CEA concentration to color intensity generated by the antibody when combined with the analyte is established. Rabbit IgG and bovine thyroid globulin are immobilized in two standard bands by using an IVEK ceramic linear pump having an accuracy of 99.95%, in amounts sufficient to give rise to a color intensity when complexed with old label antibodies corresponding to concentration of 4 and 100 ng/ml respectively CEA when such is complexed with a gold label monoclonal CEA specific antibody, an excess of which is removably deposited on the upstream fiberglass membrane. CEA specific antibody is immobilized in the test band in sufficient concentration to provide measurable color intensities when complexed with labeled CEA concentrations expected to be present in the sample. Excess of the gold label antibody against CEA gold label monoclonal antibody against rabbit IgG and gold label monoclonal antibody against bovine thyroid globulin are also removably deposited in an upstream fiberglass membrane. As in Example 1 the correlation of color intensities to antigen concentration is established using the equation Y=AX+B.

One drop of blood suspected of containing the CEA analyte, approximately 30 microliters, is added to the sample applicator site on the upstream fiberglass membrane followed by 4 drops, about 200 microliters, of a testing phosphate buffer. The fiberglass membrane used is sufficiently dense to filter out the red and white blood cells but will let the serum pass. The serum of the blood combined with buffer flows through the upstream membrane by capillary action to the label conjugate redistributing the gold antibody conjugate which then forms a complex with any analyte present in the sample. The buffer diluted serum passes from the fiberglass membrane to the porous nitrocellulose membrane and continues to flow by capillary action through the nitrocellulose membrane. Analyte gold conjugate complex is captured by the CEA antibody deposited in the test band and gives rise to a reddish color the intensity of which corresponds to the amount of analyte present in the sample. Monoclonal antibody against rabbit IgG and monoclonal antibody against Bovine thyroid globulin gold conjugate removably deposited on the fiberglass membrane and picked up by the serum are also captured by the high and low standard bands. In the presence of CEA analyte in the sample three bands of differing color intensity are obtained. After passing the test and standard bands the remaining buffered sample passes from the nitrocellulose strip to the absorption pad and is stored there. The cassette with the color bands is then inserted into a RFID reader together with the memory card containing the correlation between color intensity as measured by relative light units (RLU) and concentration of analyte. The reader employed, CHR 100, is capable of converting the color intensity into concentration using the data on the memory card. Color intensities were measured at 15 minutes after the addition of the sample and buffer. The following results are obtained:

15 Minutest Test Result:

| Analytes | CEA Concentration | RLU |
| --- | --- | --- |
| Calibrator H | 100 ng/ml | 78 |
| Calibrator L | 4 ng/ml | 21.4 |
| Sample | Y | 34.2 |

Based on the two point standard curve, the reader showed 25 ng/ml of the CEA antigen (Y) in the sample.

EXAMPLE 4

The procedure of Example 1 is repeated to determine the concentration of human Troponin-I antigen (TNI-I) in a sample using gold label monoclonal specific TNI-I antibody. The relationship of TNI-I concentration and the color intensity generated by the antibody when conjugated to the analyte is established in prior experiments. Rabbit IgG and bovine thyroid globulin are immobilized in two standard bands by using an IVEK ceramic linear pump having an accuracy of 99.95%, in amounts sufficient to give rise to a measurable color intensity corresponding to TNI-I concentrations of 1 and 50 ng/ml respectively when such is complexed with a gold label monoclonal TNI-I specific antibody. TN-I specific antibody is immobilized in the test band. Excess of the gold label antibody against TSH, gold label monoclonal antibody against rabbit IgG and gold label monoclonal antibody against bovine thyroid globulin are also removably deposited in an upstream fiberglass membrane. As in Example 1 the correlation of color intensity to antigen concentration is established using the equation Y=AX+B.

One drop of blood suspected of containing the TNI-I analyte, approximately 30 microliters, is added to the sample applicator site on the upstream fiberglass membrane followed by 4 drops, about 200 microliters, of a testing phosphate buffer. The fiberglass membrane used is sufficiently dense to filter out the red and white blood cells but will let the serum pass. The serum of the blood combined with buffer flows through the upstream membrane by capillary action to the label conjugates redistributing the gold antibody conjugates which can form a complexes with any analyte present in the sample and with the antigens in the standard band. The buffer diluted serum passes from the fiberglass membrane to the porous nitrocellulose membrane and continues to flow by capillary action through the nitrocellulose membrane. Analyte gold conjugate complex is captured by the TNI-I antibody deposited in the test band and gives rise to a reddish color the intensity of which corresponds to the amount of analyte present in the sample. Monoclonal antibodies against rabbit IgG and against bovine thyroid globulin gold conjugates removably deposited on the fiberglass membrane and picked up by the serum are captured by the high and low standard bands. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The reader employed, CHR 100 is capable of converting the color intensity into concentration using the data on the memory card. Color intensities were measured at 15 minutes after the addition of the sample and buffer. The following results are obtained:

15 Minutest Test Results:

| Analytes | TNI-I Concentration | RLU |
| --- | --- | --- |
| Calibrator H | 50 ng/ml | 62 |
| Calibrator L | 1 ng/ml | 12 |
| Sample | Y | 6 |

Based on the two point standard curve, the reader showed 0.5 ng/ml of the CEA antigen (Y) in the sample.

EXAMPLE 5

The procedure of example 5 is competitive assay procedure to determine the concentration of human Thyroxin antigen (T-4) in a blood or serum sample. In separate experiments the relationship of T-4 concentration to color intensity of the gold labeled conjugate is established. In a procedure similar to that of Example 1 rabbit IgG and bovine thyroid globulin are immobilized in two standard bands by using an IVEK ceramic linear pump having an accuracy of 99.95%, in amounts sufficient to give rise to a measurable color intensity corresponding to T-4 concentrations of 5 and 20 ng/ml respectively is when such is complexed with a gold label monoclonal (T-4) specific antibody and complexed to the antibody in the test band. Furthermore T-4 specific monoclonal antibodies are also deposited in the test band of the nitrocellulose strip. The bands are arranged such that the sample first contacts the low calibrator band showing the color intensity with the gold conjugate corresponding to 5 µg/ml of T-4 antigen, then the test band, followed by the high calibrator agent band, capable of binding the equivalent of 20 µg/ml of T-4. The deposited antigen (T-4) conjugate with bovine serum albumin in the test band are allowed to react with the gold sol conjugate of T4-antibody on the nitrocellulose and become permanently immobilized in test bands on the test membrane after reaction. The assay strip is then exposed to the gold conjugate monoclonal antibody against rabbit IgG and monoclonal antibody against bovine thyroglobulin to generate the standard color intensities from which a standard curved can be generated. The standard curve showing the correlation of color intensity with analyte concentration for different lots of assay strips is loaded into a RFID memory card. The test value may be calculated by using the equation of $Y=AX+B$ as set forth in Example 1. The test membrane is in fluid connection with an upstream non-woven fiberglass membrane onto which is deposited the antibody to the T-4 antigen conjugated to a gold label by techniques known in the art. The label conjugate is deposited down stream from where the sample to be analyzed is added to the upstream fiberglass membrane. The assay test strip also contains a sample absorption pad in fluid connection with the downstream end of the test membrane. The test strip is inserted into a cassette such as described in U.S. Pat. No. 5,821,073.

One drop of blood suspected of containing the T-4 analyte, approximately 30 microliters, is added to the sample applicator site on the upstream fiberglass membrane followed by 4 drops, about 200 microliters, of a testing phosphate buffer.

The fiberglass membrane used is sufficiently dense to filter out the red and white blood cells but will let the serum pass. The serum of the blood combined with buffer flows through the upstream membrane by capillary action to the label conjugate redistributing the gold antibody conjugate which then forms a complex with any analyte present in the sample. The buffer diluted serum passes from the fiberglass membrane to the porous nitrocellulose membrane and continues to flow by capillary action through the nitrocellulose membrane. Analyte gold conjugate complex is captured by the T-4 antibody deposited in the test band and gives rise to a reddish color the intensity of which corresponds to the amount of analyte present in the sample. The corresponding standard band gold conjugate antibodies, removably deposited on the fiberglass and picked up by the sample, are captured by the antigens in the standard bands. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The reader employed, CHR 100 is capable of converting the color intensity into concentration using the data on the memory card. Color intensities were measured at 15 minutes after the addition of the sample and buffer. The following results are obtained:
15 Minutes Test Result:

| Analytes | T-4 Concentration | RLU |
| --- | --- | --- |
| Calibrator H | 20 µg/ml | 39 |
| Calibrator L | 5 µg/ml | 79 |
| Sample | Y | 66 |

Based on the two point standard curve, the reader showed 10 µg/ml of the T-4 antigen (Y) in the sample.

EXAMPLE 6

Onto a test strip comprising a porous nitrocellulose strip (7.5 cm×0.7 cm) as the test membrane sufficient monoclonal antibody against human prostrate specific antigen (PSA) in a test band to give rise to measurable color intensity when complexed with PSA analyte color conjugates that can be expected in a sample. Rabbit IgG, bovine thyroid globulin and murine hybridoma are immobilized in three standard bands by using an IVEK ceramic linear pump having an accuracy of 99.95%, in amounts sufficient to give rise to a color intensity corresponding to a PSA concentration of 1, 5 and 10 ng/ml respectively when such is complexed with a gold label monoclonal PSA specific antibody. The test membrane is dried in a dehumidifying chamber (humidity of 10-15%) overnight. Excess of the gold label antibody against PSA, gold label monoclonal antibody against rabbit IgG, anti-mouse antibody capable of complexing with hybridoma and gold label monoclonal antibody against bovine thyroid globulin are also removable deposited in an upstream fiberglass membrane. The conjugate fiberglass pad is coated with the label conjugates, then treated with a buffer to neutralize interfering sites and then vacuum dried at 2 Torr overnight at room temperature. The pad is then cut into narrow strips (1×0.7 cm). The bands are arranged such that the sample first contacts the low and intermediate calibrator bands showing the color intensity with the gold conjugate corresponding to 1 and 5 ng/ml of PSA antigen, then the test band, followed by the high calibrator agent band, capable of binding the equivalent of 10 ng/ml of PSA. The correlation of the color density in RLU units with analyte concentration, lot #, test time, slope and intercept for the three standard bands of the particular test strip is loaded into a RFID memory card. The antigen concentrations can then be calculated using the equation $Y=AX+B$ where Y is the concentration of the analyte, X is the color intensity generated by the sample in RLU units, A is the slope of the curve obtained from the standard values and B is the intercept of the test value on the curve.

The test membrane is in fluid connection with an upstream non-woven fiberglass membrane onto which is deposited the antibody to the PSA antigen conjugated to a gold label by techniques known in the art. The label conjugate is deposited down stream from where the sample to be analyzed is added to the upstream fiberglass membrane. The assay test strip also contains a sample absorption pad in fluid connection with the downstream end of the test membrane. The test strip is inserted into a cassette such as described in U.S. Pat. No. 5,821,073.

One drop of blood suspected of containing the PSA analyte, approximately 30 microliters, is added to the sample applicator site on the upstream fiberglass membrane followed by four drops, about 200 microliters, of a commercially available phosphate buffer. The fiberglass membrane is sufficiently dense to filter out the red and white blood cells but will let the serum pass. The serum of the blood combined with buffer flows through the upstream membrane by capillary action to the label antibody conjugate location where the analyte present in the sample complexes with the gold antibody and where the buffer diluted sample picks up the antibodies of the antigens in the standard bands. The buffer diluted serum passes from the fiberglass membrane to the porous nitrocellulose membrane and continues to flow by capillary action through the nitrocellulose membrane. Analyte gold conjugate complex is captured by the PSA antibody deposited in the test band and gives rise to a reddish color the intensity of which corresponds to the amount of analyte present in the sample. Monoclonal antibody against rabbit IgG, antimouse antibody and monoclonal antibody against bovine thyroid globulin gold conjugate deposited on the fiberglass membrane and picked up by the sample are also captured by the high, intermediate and low standard bands containing sufficient calibrator agent to capture the equivalent of either one, five or ten ng/ml of analyte. In the presence of PSA analyte in the sample four bands of normally differing color intensity are obtained. After passing the test and standard bands the remaining buffered sample passes from the nitrocellulose strip to the absorption pad and is stored there. The cassette with the color bands is then inserted into a reader together with the memory card containing the correlation between color intensity as measured by relative light units (RLU) and concentration of analyte. The photo-camera reader employed, Kaiwood CHR 100, is capable of converting the color intensity into concentration using the data on the memory card. Color intensities were measured 10 and 15 minutes after the addition of the sample and buffer. Essentially the same results as obtained in Example 1 are obtained.

The invention claimed is:

1. An assay device for the quantitative determination of an analyte in a sample, comprising a test strip containing a porous test membrane allowing for capillary flow of the analyte, a porous upstream membrane in fluid connection with and located upstream from the test membrane and a porous downstream membrane in fluid connection with and located downstream from the test membrane, wherein:
   (a) the test membrane containing a test site having immobilized thereon a ligand capable of reacting with the analyte and binding the analyte to the test site, a first standard band having immobilized thereon a first calibrator agent, corresponding to a first known concentration of analyte, a second standard band having immobilized thereon a second calibrator agent corresponding to a second known concentration of analyte, and a third standard band having immobilized thereon a third calibrator agent corresponding to a known third concentration of analyte, wherein each of the first, second and third calibrator agents are capable of reacting with different label conjugates and binding the label conjugates to the first, second and third standard band sites to produce a measurable response,
   (b) the upstream membrane having a sample application site to which the sample is applied, and having a label conjugate site downstream from the sample application site having the different labeled conjugates deposited thereon, and
   (c) the downstream membrane capable of absorbing the sample and providing the capillary flow for the sample through the upstream membrane and the test membrane.

2. The assay device of claim 1, wherein the label conjugates on the upstream membrane produce a measurable response measured as a color.

3. The label conjugates of claim 1, comprising gold conjugates, fluorescent dye conjugates, latex conjugates and enzyme conjugates.

4. The assay device of claim 1, wherein the test strip is contained in a cassette allowing for the addition of the sample at the upstream membrane and viewing the results of color formation at the sites of the test membrane.

5. The assay device of claim 1, wherein the test membrane is microporous nitrocellulose and the upstream membrane is fiberglass.

6. A method for the quantitative analysis of an analyte in a sample on a test strip containing a test band, a first standard band, a second standard band and a third standard band, comprising the steps of:
   (a) immobilizing a first calibrator agent corresponding to a first known concentration of analyte to the first standard band, immobilizing a second calibrator agent corresponding to a second known concentration of analyte to the second standard band, and immobilizing a third calibrator agent corresponding to a third known concentration of analyte to the third standard band, wherein the calibrator agents are capable of conjugation with different label conjugates located on the standard bands, and further wherein the calibrator agents produce a measurable response when complexed with corresponding label conjugates,
   (b) immobilizing an antigen in the test band capable of binding the analyte when complexed to a label conjugate,
   (c) contacting the test band and the standard bands with label conjugates having known concentrations of analyte and label conjugates for the calibrator agents to form three calibrator bands, and measuring a label response from the calibrator bands,
   (d) correlating the label responses of the calibrator bands with the label responses of known concentrations of analyte label conjugates in the test band to form a standard curve,
   (e) adding a sample suspected of containing an analyte,
   (f) adding different label conjugates sufficient to generate measurable responses in the test band when complexed with any analyte present in the sample and in the standard bands,
   (g) measuring the label response at the test zone and comparing the label response to the standard curve of step (d), and
   (h) converting the measured label responses to a concentration of analyte in the sample.

7. The method of claim 6, wherein the label generates a visual signal at the binding sites of the assay device.

8. The method of claim 6, wherein the visual signal is generated by a colloidal gold conjugate, a fluorescent dye conjugate, a latex particle conjugate or an enzyme conjugate.

9. The method of claim 6, wherein the analyte is an antigen selected from the group consisting of a virus, bacterium, fungus and a prion.

10. The method of claim 6, wherein the analyte is a hormone selected from the group consisting of hCG, thyroxin, TSH, glucagons, insulin, relaxin, prolactin, melanotropin, gastrin, somatotropin, gastrin and bradykin.

11. The method of claim 6, wherein the analyte is a cancer or tumor marker selected from the group consisting of prostate specific antigen (PSA), carcinoembryonic antigen (CEA) and alpha-fetoprotein.

12. The method of claim 6, wherein the analyte is a cardiac marker.

13. The method of claim 6, wherein the calibrator agents are monoclonal ligands.

14. The method of claim 13, wherein the calibrator agents are BTG antigens, rabbit IgG antigens and the label conjugates are label bound antibodies capable of binding to the calibrator agents.

* * * * *